United States Patent [19]

Auer et al.

[11] 4,105,689
[45] Aug. 8, 1978

[54] PRODUCTION OF N-SUBSTITUTED 2-CARBAMOYL PHOSPHINIC ACIDS

[75] Inventors: Eberhard Auer; Alexander Ohorodnik, both of Erftstadt; Paul Stutzke, Bornheim-Walberberg, all of Fed. Rep. of Germany

[73] Assignee: Hoechst Aktiengesellschaft, Frankfurt am Main, Fed. Rep. of Germany

[21] Appl. No.: 845,349

[22] Filed: Oct. 25, 1977

[30] Foreign Application Priority Data

Oct. 23, 1976 [DE] Fed. Rep. of Germany ....... 2648005

[51] Int. Cl.² .............................. C07F 9/30; C07F 9/34
[52] U.S. Cl. .................................. 260/502.5; 260/543 P
[58] Field of Search .................. 260/502.5; 260/543 P

[56] References Cited

U.S. PATENT DOCUMENTS

| 2,304,156 | 12/1942 | Engelmann et al. ............. 260/502.5 |
| 2,670,369 | 2/1954 | Filatoff-Rocg et al. ........... 260/502.5 |
| 2,758,956 | 8/1956 | Shalit et al. ...................... 260/502.5 |
| 3,980,614 | 9/1976 | Noetzel et al. .................... 260/502.5 |

FOREIGN PATENT DOCUMENTS

273,196    1970    U.S.S.R. ............................... 260/543 P

OTHER PUBLICATIONS

Pudovik et al., "Chem. Abstracts", vol. 67 (1967), 32744v.
Pudovik et al., "Chem. Abstracts", vol. 72 (1970), 12830v.

*Primary Examiner*—Joseph E. Evans
*Attorney, Agent, or Firm*—Connolly and Hutz

[57] ABSTRACT

Production of N-substituted 2-carbamoyl phosphinic acids of the general formula:

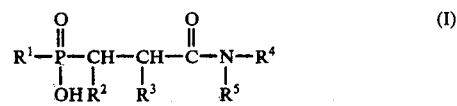

in which $R^1$ stands for an alkyl group having 1 to 4 carbon atoms or an aryl group; $R^2$ and $R^3$ stand independently of each other for an alkyl group having 1 to 4 carbon atoms, an aryl group or a hydrogen atom; $R^4$ stands for an alkyl group having 1 to 18 carbon atoms, an aryl group or a hydrogen atom; and $R^5$ stands for an alkyl group having 1 to 18 carbon atoms or an aryl group. More specifically, a 2-chloroformyl phosphinic acid chloride of the general formula

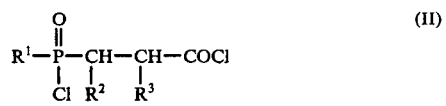

is reacted at 120° to 170° C with an amine of the general formula

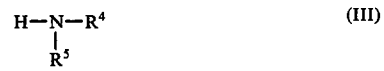

and resulting N-substituted 2-carbamoyl phosphinic acid chloride of the general formula

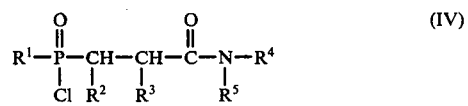

the latter compound being obtained while hydrogen chloride is split off, is hydrolyzed with water.

6 Claims, No Drawings

PRODUCTION OF N-SUBSTITUTED 2-CARBAMOYL PHOSPHINIC ACIDS

This invention relates to a process for making N-substituted 2-carbamoyl phosphinic acids of the general formula:

$$R^1-\underset{\underset{OH}{|}}{\overset{\overset{O}{\|}}{P}}-\underset{\underset{R^2}{|}}{CH}-\underset{\underset{R^3}{|}}{CH}-\overset{\overset{O}{\|}}{C}-\underset{\underset{R^5}{|}}{N}-R^4 \quad (I)$$

in which $R^1$ stands for an optionally substituted alkyl group having 1 to 4 carbon atoms or an optionally substituted aryl group; $R^2$ and $R^3$ each stand independently of each other for an optionally substituted alkyl group having 1 to 4 carbon atoms, an optionally substituted aryl group or a hydrogen atom; $R^4$ stands for an optionally substituted alkyl group having 1 to 18 carbon atoms, an optionally substituted aryl group or a hydrogen atom; and $R^5$ stands for an optionally substituted alkyl group having 1 to 18 carbon atoms or an optionally substituted aryl group, which process comprises: reacting, at a temperature of 120° to 170° C, a 2-chloroformyl phosphinic acid chloride of the general formula $$R^1-\underset{\underset{Cl}{|}}{\overset{\overset{O}{\|}}{P}}-\underset{\underset{R^2}{|}}{CH}-\underset{\underset{R^3}{|}}{CH}-COCl \quad (II)$$

with an amine of the general formula $$H-\underset{\underset{R^5}{|}}{N}-R^4 \quad (III)$$

and hydrolyzing with water the resulting N-substituted 2-carbamoyl phosphinic acid chloride of the general formula $$R^1-\underset{\underset{Cl}{|}}{\overset{\overset{O}{\|}}{P}}-\underset{\underset{R^2}{|}}{CH}-\underset{\underset{R^3}{|}}{CH}-\overset{\overset{O}{\|}}{C}-\underset{\underset{R^5}{|}}{N}-R^4 \quad (IV)$$

the latter compound being obtained while hydrogen chloride is split off.

It is known that N-substituted 2-carbamoyl-phosphinic acids of general formula (I) can be made by reacting a pholane derivative of the general formula $$R^1-\overset{\overset{O}{\|}}{P}\underset{O}{\overset{}{\diagdown}}\underset{\underset{\underset{\|}{O}}{C}}{\diagup}\underset{\underset{}{CH-R^3}}{\overset{CH-R^2}{}} \quad (V)$$

with an amine of the general formula $$H-\underset{\underset{R^5}{|}}{N}-R^4 \quad (III)$$

in which $R^1$ through $R^5$ have the meanings given hereinabove.

As described, e.g., by V. K. Khairullin et al. (C.A. 67, 54 222a (1967)), it is possible to produce [2-(phenylcarbamoyl-)ethyl-]-methyl phosphinic acid of the general formula $$CH_3-\overset{\overset{O}{\|}}{P}\underset{O}{\overset{}{\diagdown}}\underset{\underset{\underset{\|}{O}}{C}}{\diagup}\underset{\underset{}{CH_2}}{\overset{CH_2}{}} + H_2N-C_6H_5 \longrightarrow$$

$$CH_3-\underset{\underset{OH}{|}}{\overset{\overset{O}{\|}}{P}}-CH_2-CH_2-\overset{\overset{O}{\|}}{C}-NH-C_6H_5.$$

from 2-methyl-2,5-dioxo-1-oxa-2-phospholane and aniline.

It has also been described by V. K. Khairullin et al. (C.A. 69 106816k (1968)) that [2-(phenylcarbamoyl)-2-(methyl)-ethyl]-methyl phosphinic acid of the formula $$CH_3-\overset{\overset{O}{\|}}{P}\underset{O}{\overset{}{\diagdown}}\underset{\underset{\underset{\|}{O}}{C}}{\diagup}\underset{\underset{}{CH-CH_3}}{\overset{CH_2}{}} + H_2NC_6H_5 \longrightarrow$$

$$CH_3\overset{\overset{O}{\|}}{P}-CH_2-\underset{\underset{CH_3}{|}}{CH}-\overset{\overset{O}{\|}}{C}-NH-C_6H_5.$$
$$\underset{OH}{|}$$

can be made from 2,4-dimethyl-2,5-dioxo-1-oxa-2-phospholane and aniline.

V. K. Khairullin et al. (C.A. 71, 39082 u (1969)) has also described that [2-(phenylcarbamoyl-) ethyl-]-chloroformyl phosphinic acid of the following formula $$Cl-CH_2-\overset{\overset{O}{\|}}{P}\underset{O}{\overset{}{\diagdown}}\underset{\underset{\underset{\|}{O}}{C}}{\diagup}\underset{\underset{}{CH_2}}{\overset{CH_2}{}} + H_2N-C_6H_5 \longrightarrow$$

$$Cl-CH_2-\underset{\underset{OH}{|}}{\overset{\overset{O}{\|}}{P}}-CH_2-CH_2-\overset{\overset{O}{\|}}{C}-NH-C_6H_5$$

is obtainable from 2-chloromethyl-2,5-dioxo-1-oxa-2-phospholane and aniline.

As disclosed in German Patent Specification "Offenlegungsschrift" No. 2,511,185, Example 1, [2-(2,4,6-tribromophenylcarbamoyl-)ethyl-]-methyl phosphinic acid of the following formula

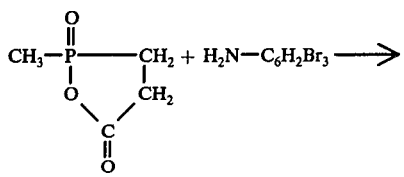

$$CH_3-\underset{\underset{O}{|}}{\overset{\overset{O}{\|}}{P}}-CH_2-CH_2-\overset{O}{\overset{\|}{C}}-NH-C_6H_2Br_3$$
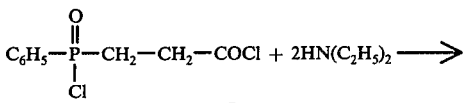

is obtainable from 2-methyl-2,5-dioxo-1-oxa-2-phospholane and 2,4,6-tribromo-aniline.

This is the only known process which can generally be used for making N-substituted 2-carbamoyl-phosphinic acids, but which is not suitable for use in the production of relatively large quantities of these compounds, for the following reasons. Even at 180° C, the reaction velocity is so low that several hours are needed to complete the reaction. On the other hand, as a result of the high reaction temperature, both the phospholane and 2-carbamoyl phosphinic acid are subjected to prolonged thermal stress so that they are liable to undergo decomposition which adversely affects the coloration and yield of the final product.

These disadvantageous effects are avoided in the process of the present invention.

In accordance with the present invention, the reaction should more preferably be effected at temperatures of 140° to 150° C. A further feature of the present invention provides for the compound of formula (IV) to be hydrolyzed either in water alone or with the use of water or in a solvent miscible with water.

The radicals R¹ through R⁵ may more preferably stand for a methyl, chloromethyl or ethyl group, and the aryl group preferably is a phenyl, naphtyl or 2,4,6-tribromophenyl group.

The fact that it is possible under the conditions employed in the present process to produce a phosphinic acid chloride of formula (IV) from a 2-chloroformyl-phosphinic acid chloride of formula (II) and an amine of formula (III) is a result which would not have been expected in view of the prior art. In the literature, the reaction of a 2-chloroformyl-phosphinic acid chloride of formula (II) with an amine of formula (III) has been held to also involve the reaction of the two acid chloride groups in the 2-chloroformyl-phosphinic acid chlorides.

Thus, for example, A. N. Pudovik et al. (C.A. 72, 12830 v (1970)) obtained 1,2-diphenyl-2,5-dioxo-1-aza-2-phospholane of the formula $$C_6H_5-\underset{\underset{Cl}{|}}{\overset{\overset{O}{\|}}{P}}-CH_2-CH_2-COCl + H_2N-C_6H_5 \longrightarrow$$

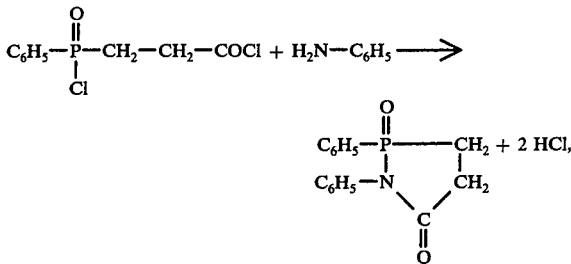

by reacting [2-(chloroformyl-)ethyl-]phenyl phosphinic acid chloride with aniline at a relatively low temperature which however made it necessary to sequester the hydrogen chloride set free by means of triethylamine.

In an analogous reaction effected with diethylamine and the addition of triethylamine as an acid-sequestering agent, A. N. Pudovnik et al. (C.A. 67, 32744 v (1967)) obtained [2-(diethylcarbamoyl-)ethyl]phenyl phosphinic acid diethyl amide $$C_6H_5-\underset{\underset{Cl}{|}}{\overset{\overset{O}{\|}}{P}}-CH_2-CH_2-COCl + 2HN(C_2H_5)_2 \longrightarrow$$

$$C_6H_5-\underset{\underset{N(C_2H_5)_2}{|}}{\overset{\overset{O}{\|}}{P}}-CH_2-CH_2-CO-N(C_2H_5)_2 + 2HCl.$$

A further unexpected and beneficial result of the present process resides in the fact that the hydrogen chloride set free under the conditions used in accordance with this invention escapes in gaseous form, so that it is not necessary for it to be sequestered by means of an auxiliary base. As can be inferred from this, the present process takes place as shown by the following empirical reaction equation

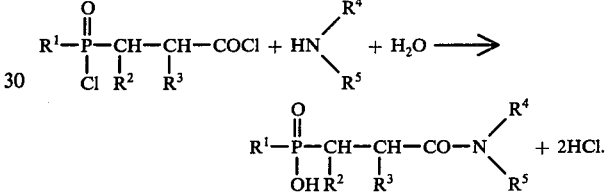

This reaction is effected in two steps, the first step comprising effecting the reaction under the conditions described to the stage of the N-substituted 2-carbamoyl phosphinic acid chloride of formula (IV), which is an intermediary product of the present process.

The reaction of the 2-chloroformyl phosphinic acid chlorides of formula (II) with the amines of formula (III) is effected at a temperature which should be selected so as to comply with certain requirements. More specifically, it is preferable to operate at a temperature which permits the reaction medium to be maintained in the liquid phase during the entire reaction period. Speaking generally, temperatures higher than 120° C are normally necessary to initiate dehydrochlorination. In the presence of an excess of amine, the dehydrochlorination is however liable to be initiated even at a lower temperature. In this event, the corresponding substituted ammonium hydrochloride is obtained in the form of a salt-like solid compound, whereby the reaction is rendered difficult. It is therefore good practice to effect the reaction at a temperature which is higher than the cleavage temperature of the corresponding substituted ammonium hydrochloride. The temperature which should preferably be employed is easy to determine by preliminary tests, and it should be the higher the stronger the basicity of the amine used.

The reaction is easy to carry out, for example, by introducing the amine, if desired in the form of a melt, at about 120° to 140° C, into an agitator-provided vessel and admixing it therein with the 2-chloroformyl phosphinic acid chloride, which may also be used in liquid form. Especially in those cases, in which the reaction initially produces a substituted ammonium hydrochloride, the reaction mixture will be found to warm up under the reaction heat evolved. The temperature is then maintained at a desired level. In view of the fact that the dehydrochlorination commonly involves a loss of heat, it is necessary for the reaction temperature to be maintained by supplying heat from the outside.

In carrying out the present process, it is not necessary to employ a solvent or diluent, the reaction product itself being used as the reaction medium, especially during continuous operation.

The second step comprises hydrolyzing the 2-carbamoyl phosphinic acid chlorides of formula (IV), which are obtained as intermediates in the present process, so as to produce the desired N-substituted 2-carbamoyl phosphinic acids of formula (I).

The hydrolyzing step may be effected by methods commonly used for hydrolyzing an acid chloride. The particular method to be used in a given case is selected in accordance with the properties desired for the final product.

In those cases, in which the particular 2-carbamoyl phosphinic acid concerned is, e.g., water-insoluble or water-insoluble at a given pH, the hydrolysis is easy to effect by pouring the reaction mixture into water and finely distributing it therein with agitation. In this case, the water-insoluble phosphinic acid can readily be recovered by filtration, if desired after adjustment of an appropriate pH-value.

In other cases it is possible to effect the hydrolysis, e.g., in an organic solvent miscible with water, the latter being used in stoichiometric proportions or in excess.

The N-substituted 2-carbamoyl phosphinic acids obtainable by the present process are suitable for use as flame-retardant agents in polymeric moulding compositions (cf. German Patent Specification "Offenlegungsschrift No. 2,511,185).

The following Examples illustrate the invention which is however not limited thereto.

EXAMPLE 1

Production of

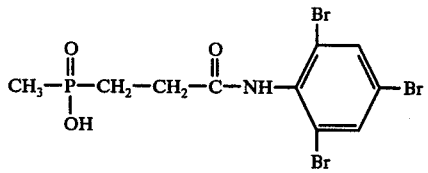

[2-(2,4,6-tribromophenylcarbamoyl-)ethyl-]methyl phosphinic acid.

330 g (1 mol) of 2,4,6-tribromoaniline was placed in a 2 liter three-necked flask provided with a short distilling column which had a heatable dropping funnel vertically, and a reflux condenser laterally, mounted thereon, and heated in an oil bath to 140° C therein. The dropping funnel was heated to 70° C and 193 g (1.02 mol) of [2-(chloroformyl-)ethyl-]-methyl phosphinic acid chloride (prepared as described by V. K. Khairullin et al., C.A. 67, 54222 a (1967)) was added dropwise within 20 minutes with thorough agitation. Sublimate was washed out in the distilling column and rewashed into the flask. The temperature inside the flask rose to 150° C and was maintained. A vigorous stream of HCl escaped through the reflux condenser mounted laterally on the distilling column. The HCl was admixed with some nitrogen and absorbed in water. After all had been dropped in, the whole was allowed to stand for 10 minutes at 150° C, whereupon considerably less HCl was found to escape. The water was subjected to alkalimetric titration and found to contain altogether 1.05 mol of acid.

Next, the reaction melt was poured with thorough agitation and with the use of a mixing device into 4 liter of cold water. A white precipitate of [2-(2,4,6-tribromophenyl-carbamoyl)-ethyl-]methyl phosphinic acid was obtained. It was filtered off and dried at 80° C under vacuum.

The yield was 410 g (88% of the theoretical, based on 2,4,6tribromoaniline). The product had a melting point of 248° C and a specimen of it, prepared in the manner described in German Patent Specification "Offenlegungsschrift" No. 2,511,185, Example 1, had a mixed melting point of 249° C.

EXAMPLE 2

Preparation of

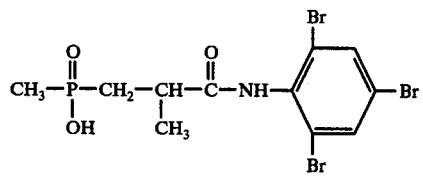

[2-(2,4,6-tribromophenylcarbamoyl-)2-(methyl)-ethyl-]phosphinic acid.

330 g (1 mol) of 2,4,6-tribromoaniline was reacted as described in Example 1 with 207 g (1.02 mol) of [2-(chloroformyl-)2-(methyl)ethyl-]methyl phosphinic acid chloride (prepared as described by V. K. Khairullin et al., C.A. 69, 106816 k (1968)). After hydrolysis with 6 liters of water, the resulting [2-(2,4,6-tribromophenylcarbamoyl-)2-(methyl)ethyl-]methyl phosphinic acid was filtered off and dried at 80° C under vacuum.

The yield was 434 g (90% of the theoretical, based on 2,4,6-tribromoaniline). The product had a melting point of 246° C.

| | Analysis: (C₁₁H₁₃Br₃NO₃P) | | | | |
|---|---|---|---|---|---|
| | C | H | Br | N | P |
| Calculated: | 27.65 | 2.74 | 50.16 | 2.93 | 6.48 weight % |
| Found: | 27.7 | 3.0 | 49.4 | 3.0 | 6.4 |

EXAMPLE 3

Preparation of

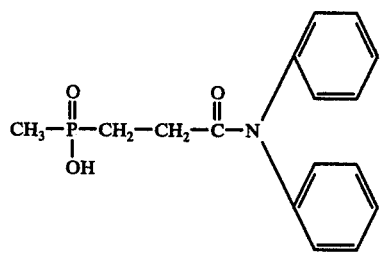

([2-(diphenylcarbamoyl)-ethyl-]methyl phosphinic acid)

As described in Example 1, 169 g (1 mol) of diphenylamine was reacted with 193 g (1.02 ) of [2-(chloroformyl-ethyl-]methyl phosphinic acid chloride. The temperature inside the flask rose to 165° C. This was accompanied by a vigorous evolution of HCl. During the reaction, the temperature dropped to 150° C. After the evolution of HCl had died down, the melt was dissolved in a mixture of 500 ml of dimethylformamide and 40 ml of water, and the solution was heated to the boil for about 1 hour. Next, the solvent was distilled off and the remaining crystalline magma was washed out with 50 ml of acetone. After filtration, [2-(diphenylcarbamoyl-)ethyl-]methyl phosphinic acid was obtained in a yield of 207 g (75% of the theoretical, based on diphenylamine).

The product had a melting point of 154°–156° C.

| Analysis: ($C_{16}H_{17}NO_3P$) | | | |
|---|---|---|---|
| C | H | N | P |
| Calculated: 63.57 | 5.67 | 4.63 | 10.25 weight % |
| Found: 62.8 | 5.7 | 4.6 | 10.0 weight % |

We claim:

1. A process for making N-substituted 2-carbamoyl phosphinic acids of the general formula:

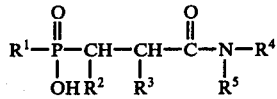 (I)

in which $R^1$ stands for an alkyl group having 1 to 4 carbon atoms or an aryl group; $R^2$ and $R^3$ stand independently of each other for an alkyl group having 1 to 4 carbon atoms, an aryl group or a hydrogen atom; $R^4$ stands for an alkyl group having 1 to 18 carbon atoms, an aryl group or a hydrogen atom; and $R^5$ stands for an alkyl group having 1 to 18 carbon atoms or an aryl group, which process comprises:

reacting, at a temperature of 120° to 170° C, a 2-chloroformyl phosphinic acid chloride of the general formula

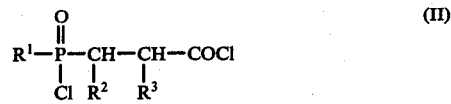 (II)

with an amine of the general formula

 (III)

and hydrolyzing with water the resulting N-substituted 2-carbamoyl phosphonic acid chloride of the general formula

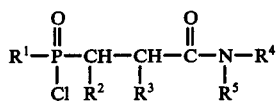

the latter compound being obtained while hydrogen chloride is split off.

2. A process as claimed in claim 1, wherein the reaction is effected at a temperature of 140° to 150° C.

3. A process as claimed in claim 1, wherein the hydrolysis is effected in water.

4. A process as claimed in claim 1, wherein the hydrolysis is effected in a solvent miscible with water.

5. A process as claimed in claim 1, wherein at least one of the radicals $R^1$, $R^2$, $R^3$, $R^4$, and $R^5$ stands for a substituted alkyl radical.

6. A process as claimed in claim 1, wherein at least one of the radicals $R^1$, $R^2$, $R^3$, $R^4$ and $R^5$ stands for a substituted aryl radical.

* * * * *